United States Patent
Saint-Loup et al.

(10) Patent No.: US 12,398,235 B2
(45) Date of Patent: Aug. 26, 2025

(54) OLIGOMERIC EPOXY PRE-POLYMERS COMPRISING ISOSORBIDE UNITS

(71) Applicant: ROQUETTE FRERES, Lestrem (FR)

(72) Inventors: René Saint-Loup, Lomme (FR); Théodore Vanbesien, Armentières (FR)

(73) Assignee: Roquette Freres, Lestrem (FR)

(*) Notice: Subject to any disclaimer, the term of this patent is extended or adjusted under 35 U.S.C. 154(b) by 224 days.

(21) Appl. No.: 18/251,156

(22) PCT Filed: Nov. 3, 2021

(86) PCT No.: PCT/EP2021/025427
§ 371 (c)(1),
(2) Date: Apr. 28, 2023

(87) PCT Pub. No.: WO2022/096148
PCT Pub. Date: May 12, 2022

(65) Prior Publication Data
US 2024/0010785 A1    Jan. 11, 2024

(30) Foreign Application Priority Data
Nov. 3, 2020 (FR) ..................... 2011271

(51) Int. Cl.
*C08G 59/26* (2006.01)
*C08G 59/04* (2006.01)

(52) U.S. Cl.
CPC ............. *C08G 59/26* (2013.01); *C08G 59/04* (2013.01)

(58) Field of Classification Search
None
See application file for complete search history.

(56) References Cited

U.S. PATENT DOCUMENTS

| | | | |
|---|---|---|---|
| 3,041,300 A | 6/1962 | Morrison | |
| 3,272,845 A | 9/1966 | Zech et al. | |
| 4,770,871 A | 9/1988 | Greenshields | |
| 2008/0009599 A1* | 1/2008 | East | C07D 493/04 528/1 |
| 2015/0307650 A1 | 10/2015 | Hammond et al. | |
| 2017/0002132 A1* | 1/2017 | Buffe | C08G 59/5026 |
| 2017/0183532 A1* | 6/2017 | Park | C09D 5/00 |
| 2019/0055401 A1* | 2/2019 | Chang | C08L 69/00 |
| 2020/0307109 A1* | 10/2020 | Gherardi | C08G 59/26 |
| 2024/0010785 A1* | 1/2024 | Saint-Loup | C08G 59/26 |

FOREIGN PATENT DOCUMENTS

| | | |
|---|---|---|
| EP | 3647335 A1 | 5/2020 |
| WO | 2008/147472 A1 | 12/2008 |
| WO | 2008/147473 A1 | 12/2008 |
| WO | 2012/157832 A1 | 11/2012 |
| WO | 2013164743 A1 | 11/2013 |
| WO | 2015110758 A1 | 7/2015 |
| WO | 2019122257 A1 | 6/2019 |

* cited by examiner

*Primary Examiner* — Megan McCulley

(57) ABSTRACT

The invention relates to an epoxy pre-polymer comprising isosorbide units, characterized in that it comprises less than 1% by weight of isosorbide diglycidyl ether relative to the total weight of the epoxy pre-polymer. The invention also relates to a method for producing such an epoxy pre-polymer.

14 Claims, No Drawings

OLIGOMERIC EPOXY PRE-POLYMERS COMPRISING ISOSORBIDE UNITS

TECHNICAL FIELD

The present disclosure relates to the field of polyepoxides and relates in particular to epoxy pre-polymers comprising isosorbide units as well as methods for preparing same. More particularly, the present disclosure relates to epoxy pre-polymers comprising isosorbide units rich in oligomers and poor in monomers and in short-chain oligomers.

PRIOR ART

Polyepoxides, also called epoxide polymers, or commonly called "epoxy", are widely used, equally as a surface material, for example, for manufacturing adhesives or coatings, and as structural materials, for example, as a matrix of composite materials.

Polyepoxides are obtained by curing curable compositions comprising an epoxy pre-polymer.

Within the meaning of the present invention, an epoxy pre-polymer is a composition comprising a single compound (that is, a set of identical molecules) comprising epoxide functions or a mixture of different compounds comprising epoxide functions, the said compound(s) being capable of participating in subsequent polymerization resulting in the obtaining of a polyepoxide.

The compounds comprising epoxide functional groups comprised in an epoxy pre-polymer may or may not comprise an oligomeric fraction. They may or may not comprise a polymeric fraction. An epoxy pre-polymer may result from the mixing of a first epoxy pre-polymer with a reactive diluent.

Most of the curable compositions comprising epoxy pre-polymers that are especially used for manufacturing adhesives, coatings, or matrices for composite materials contain, besides epoxy pre-polymers, at least one curing agent and/or at least one accelerating agent.

When curing the curable composition comprising an epoxy pre-polymer, opening reactions for the epoxide functional groups of the epoxy pre-polymer allow the formation of chemical bonds between compounds comprised in the epoxy pre-polymer (referred to as "homopolymerization of the epoxy pre-polymer") and/or between a compound comprised in the epoxy pre-polymer and a curing agent. This results in the formation of a three-dimensional macromolecular network.

The term "accelerating agent" means compounds that make it possible to catalyze the homopolymerization reaction between compounds comprised in the epoxy pre-polymer or the reaction between a compound comprised in the epoxy pre-polymer and a curing agent. Lewis acids, Lewis bases and photoinitiators are examples thereof.

The term "curing agent" is understood to mean any compound different from the epoxy pre-polymer allowing a three-dimensional network to be formed by reacting with the epoxide functions of said pre-polymer. The amines, amido-amines, Mannich bases, organic acids (including polyesters terminated by carboxylic functions), organic acid anhydrides, latent curing agents (of the cyanamide, imidazole type, etc.) are examples thereof.

In single-component curable compositions, accelerating agents and/or curing agents are directly incorporated into the epoxy pre-polymer: reference is made to 1K systems. In two-component curable compositions, the accelerating agent and/or the curing agent is/are packaged separately from the epoxy pre-polymer and mixing only occurs when the curable composition is applied and shaped: reference is made to 2K systems.

Curable compositions comprising an epoxy pre-polymer may also contain organic or inorganic fillers (silica, sand, aluminum oxide, talc, calcium carbonate, etc.), pigments, plasticizers, stabilizers, thixotropic agents.

Bisphenol A diglycidyl ether (BADGE), of formula (i), is a chemical compound that is currently very widely used as an epoxy prepolymer.

[Chem. 1]

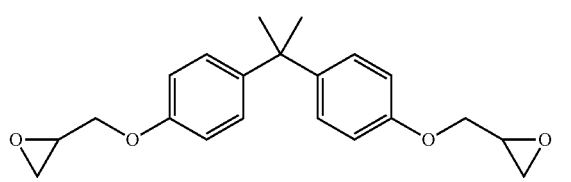

(i)

BADGE is a product obtained from petroleum, which is a disadvantage within a context of increasing prices and/or scarcity of petroleum resources.

Furthermore, bisphenol A is currently acknowledged as being and endocrine disruptor.

This potentially makes the handling of epoxy prepolymers based on bisphenol A or contact with the polyepoxides obtained from BADGE potentially hazardous to health.

For some years it has been known that BADGE may be replaced by mixtures comprising isosorbide diglycidylether (IDGE), which is a biosourced product obtained from isosorbide.

The structure of isosorbide (formula (ii)) is represented below:

[Chem 2]

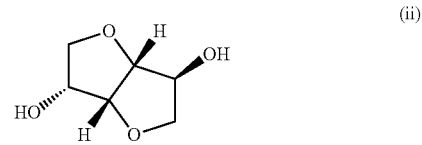

(ii)

Subsequently, the representation of the stereochemistry in the isosorbide units will be omitted.

The structure of IDGE (formula (iii)) is represented below:

[Chem. 3]

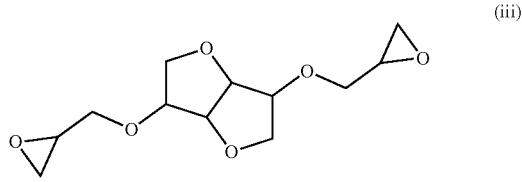

(iii)

Today, this compound is widely known and described in the literature, as is the method for its synthesis. For example, documents U.S. Pat. Nos. 3,272,845, 4,770,871, WO2008/147472, WO2008/147473, U.S. Pat. No. 3,041,300, WO2012/157832 and WO2015/110758 can be cited, which disclose methods for synthesizing IDGE.

An entire field of research has thus emerged with a view to allowing the industrial use of IDGE and more generally of epoxy pre-polymers comprising isosorbide units.

However, it has recently appeared to the applicant that epoxy pre-polymers comprising isosorbide units heretofore developed have mutagenic properties. To the best of the applicant's knowledge, these mutagenic properties were not known elsewhere.

Continuing its research, the applicant ultimately found that by increasing the molar mass of the epoxy pre-polymers comprising isosorbide units, it could be possible to reduce or even eliminate their mutagenic potential. This surprising effect is at the basis of the present invention.

SUMMARY

The present disclosure relates to epoxy pre-polymers comprising isosorbide units, the mutagenic potential of which is reduced or suppressed.

An epoxy pre-polymer is thus proposed comprising isosorbide units, characterized in that it comprises less than 1% by weight, relative to the total weight of the epoxy pre-polymer, of IDGE.

According to another aspect, a curable composition is proposed comprising an epoxy pre-polymer according to the invention, further comprising at least one accelerating agent and/or at least one curing agent.

According to another aspect, a polyepoxide is proposed, obtained by curing a curable composition according to the invention.

According to another aspect, a composite material, a coating or an adhesive comprising a polyepoxide according to the invention is proposed.

According to another aspect, a method for preparing an epoxy pre-polymer according to the invention, comprising the following steps is proposed:

a step a) of providing an epoxy pre-polymer A comprising isosorbide units;

optionally, a step b) and/or a step c), step b) being able to be carried out before step c) or vice versa;

a step d) carried out after any one of the steps a), b) or c);

wherein step b) comprises a step of reaction between a polyol and the epoxy pre-polymer A or the epoxy pre-polymer C obtained at the end of step c) or the epoxy pre-polymer D obtained at the end of step d) so as to obtain an epoxy pre-polymer B comprising isosorbide units of Mn greater than that of the epoxy pre-polymer A, C or D respectively, wherein step c) comprises a step of refunctionalizing the epoxy pre-polymer A or the epoxy pre-polymer B or the epoxy pre-polymer D obtained at the end of step d) so as to obtain an epoxy pre-polymer C comprising isosorbide units having an EEW less than that of the epoxy pre-polymer A, B or D respectively, wherein step d) comprises a step of purification of the epoxy pre-polymer A, B or C making it possible to reduce the isosorbide diglycidyl ether content of the epoxy pre-polymer A, B or C).

According to another aspect, an alternative method for preparing an epoxy pre-polymer comprising isosorbide units, comprising the following steps, is proposed:

e) a step of providing a $1^{st}$ epoxy pre-polymer devoid of isosorbide units;

f) a step of reaction between the $1^{st}$ epoxy pre-polymer and isosorbide so as to obtain a $2^{nd}$ epoxy pre-polymer comprising isosorbide and Mn units greater than that of the $1^{st}$ epoxy pre-polymer;

g) optionally a step of refunctionalizing the $2^{nd}$ epoxy pre-polymer so as to obtain a $3^{rd}$ epoxy pre-polymer having an EEW less than that of the $2^{nd}$ epoxy pre-polymer.

Further features and benefits of the present invention will become apparent from reading the following detailed description.

DETAILED DESCRIPTION

In the present document, the expression "comprised between . . . and . . . " should be understood to include the limit values.

In the present document, the term "glycidyl ether group" denotes the group whose structure is represented below (formula (iv)):

[Chem 4]

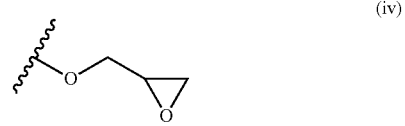

(iv)

In the present document, the term "isosorbide unit" denotes the group whose structure is represented below (formula (v)):

[Chem 5]

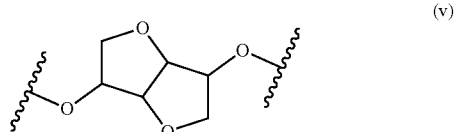

(v)

In the present document, a glycidyl ether group carried by an isosorbide unit has the following structure (formula vi):

[Chem 6]

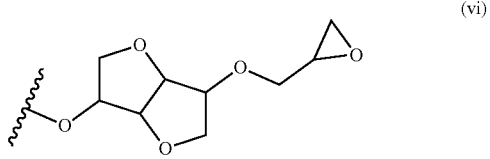

(vi)

When any one of the IDGE synthesis methods described in documents U.S. Pat. Nos. 3,272,845, 4,770,871, WO2008/147472, WO2008/147473, U.S. Pat. No. 3,041,300, WO2012/157832 and WO2015/110758 is implemented, an epoxy pre-polymer comprising isosorbide monoglycidyl ether (IMGE) is in fact obtained, as are oligomers comprising isosorbide units and glyceryl units.

In the present document, the term "glyceryl unit" denotes the group whose structure is represented below (formula (vii)):

[Chem 7]

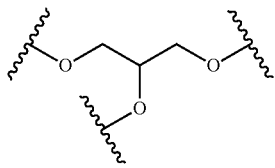

(vii)

These oligomers may comprise one or several glycidyl ether moieties carried by isosorbide units and/or glyceryl units.

By way of examples, the structure of two oligomers which are sometimes present in epoxy pre-polymers comprising IDGE are represented below.

Thus, the following oligomer will be called in the present document diglycidyl ether diisosorbide glyceryl (DGEDIG; formula (viii)):

[Chem 8]

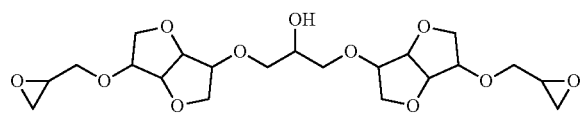

(viii)

And the following oligomer will be called in the present document diglycidyl ether triisosorbide diglyceryl (DGET-IDG; formula (ix)):

[Chem 9]

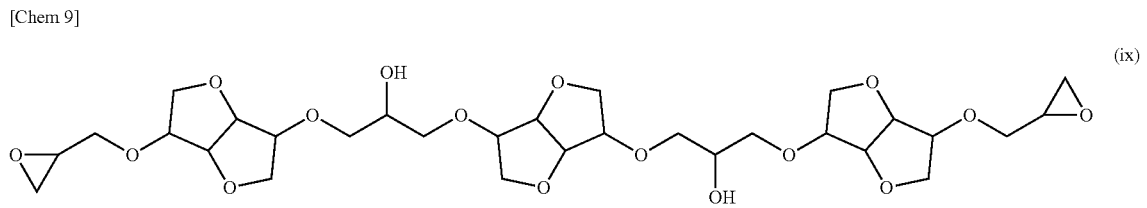

(ix)

In the present document, the term "epoxy pre-polymer based on an alcohol" refers to as an epoxy pre-polymer wherein the epoxide functions are essentially comprised in glycidyl ether groups, and wherein at least 5% of the glycidyl ether groups are borne by units of said alcohol or by glyceryl units that themselves are bonded to units of said alcohol.

For example, in an isosorbide-based epoxy pre-polymer, at least 5% of the glycidyl ether groups are borne by isosorbide units and glyceryl units bonded to isosorbide units. These glycidyl ether groups are present, for example, within IMGE, within IDGE, within glycidyl ether-isosorbide units comprised in oligomers, or within glycidyl ether-glyceryl-isosorbide units comprised in oligomers.

An example of a glycidyl ether-glyceryl-isosorbide unit is represented below (formula x):

[Chem 10]

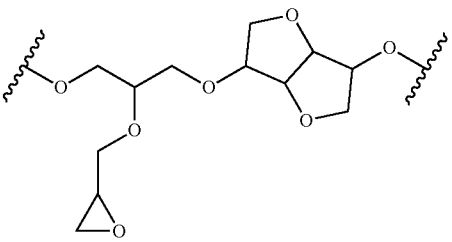

(x)

The epoxy pre-polymers obtained by implementing the methods for synthesizing IDGE described in the documents cited above are epoxy pre-polymers based on isosorbide.

An epoxy pre-polymer may also be based on several alcohols. For example, an epoxy pre-polymer based on an alcohol 1 and an alcohol 2 is an epoxy pre-polymer wherein the epoxide functions are essentially comprised in glycidyl ether groups and wherein, at least 5% of the glycidyl ether groups are carried by said alcohol 1 units or by glyceryl units which themselves are bound to units said alcohol 1 and wherein, at least 5% of the glycidyl ether groups are carried by said alcohol 2 units or by glyceryl units which themselves are bonded to said alcohol 2 units.

In the present application, the term "polyepoxide based on an alcohol" refers to a polyepoxide obtained by curing a curable composition comprising an epoxy pre-polymer based on said alcohol.

The epoxy equivalent by weight (EEW) of an epoxy pre-polymer is defined as the mass of epoxy pre-polymer containing one mole of glycidyl ether groups. For example, pure IDGE (formula ii), which has a molar mass of 258 g/mol and which contains 2 glycidyl ether groups, has an EEW of 129 g/eq.

In an epoxy prepolymer based on a diol, the EEW is minimal if said epoxy prepolymer is diglycidyl ether of said pure diol. Generally, the EEW of a diol-based epoxy pre-polymer increases when the content of oligomer and/or of mono-glycidyl ether of said diol increases in said epoxy pre-polymer.

Using epoxy pre-polymers having low EEW, polyepoxides are obtained with a three-dimensional network having a high crosslinking density. A higher node density allows a material to be obtained that has a higher glass transition temperature (Tg) and is more chemically and mechanically resistant.

An epoxy pre-polymer is proposed comprising isosorbide units, characterized in that it comprises less than 1%, preferably less than 0.5%, more preferentially less than 0.1% by weight of IDGE relative to the total weight of the epoxy pre-polymer.

Thus, unlike epoxy pre-polymers comprising isosorbide units of the prior art for which a high IDGE content is desired, the epoxy pre-polymers according to the invention have a low IDGE content.

This makes it possible to lower their mutagenic potential as shown by the tests described in the "examples" part of the present document.

According to one embodiment, the epoxy pre-polymer according to the invention comprises less than 1% by weight of IDGE relative to the total weight of the epoxy pre-polymer and less than 1%, preferably less than 0.5%, more preferentially less than 0.1% by weight of IMGE relative to the total weight of the epoxy pre-polymer.

For example, the epoxy pre-polymer according to the invention comprises less than 0.5% by weight of IDGE relative to the total weight of the epoxy pre-polymer and less than 1%, preferably less than 0.5%, more preferentially less than 0.1% by weight of IMGE relative to the total weight of the epoxy pre-polymer.

For example, the epoxy pre-polymer according to the invention comprises less than 0.1% by weight of IDGE relative to the total weight of the epoxy pre-polymer and less than 1%, preferably less than 0.5%, more preferentially less than 0.1% by weight of IMGE relative to the total weight of the epoxy pre-polymer.

Preferably, in the epoxy pre-polymer according to the invention, the compounds comprising isosorbide units having a molar mass of less than 300 g/mol, preferably less than 500 g/mol, more preferentially less than 800 g/mol, represent less than 1% by weight relative to the total weight of the pre-polymer.

For example, in the epoxy pre-polymer according to the invention, the compounds comprising isosorbide units having a molar mass of less than 300 g/mol, preferably less than 500 g/mol, more preferentially less than 800 g/mol, represent less than 0.5% by weight relative to the total weight of the pre-polymer.

For example, in the epoxy pre-polymer according to the invention, the compounds comprising isosorbide units having a molar mass of less than 300 g/mol, preferably less than 500 g/mol, more preferentially less than 800 g/mol, represent less than 0.1% by weight relative to the total weight of the pre-polymer.

Compounds different from IDGE having low molar masses, for example less than 800 g/mol, comprising isosorbide units and which are generally present in epoxy pre-polymers comprising isosorbide units could also have a relatively high mutagenic potential. Most probably, among these compounds, the closer their structure (and therefore their molar mass) is to that of IDGE, the closer their mutagenic potential will be to that of IDGE. Conversely, for compounds heavier than IDGE, the higher their molar mass, the lower the mutagenic potential.

Among the compounds with molar masses of less than 800 g/mol, compounds comprising one, two or three isosorbide units, the structure of which is close to that of IDGE (which has a molar mass of 258.3 g/mol), may be found.

Among compounds with molar masses of less than 300 g/mol, compounds comprising 1 isosorbide unit, for example IMGE, may be found.

Among the compounds with molar masses of less than 500 g/mol, compounds comprising 2 isosorbide units, for example DGEDIG, which has a molar mass of 460.5 g/mol, may be found.

Among the compounds with molar masses of less than 800 g/mol, compounds comprising 3 isosorbide units, for example DGETIDG, which has a molar mass of 662.7 g/mol, may be found.

It is possible to verify that the compositions obtained do not comprise IDGE or other compounds with a molar mass of less than 800 g/mol by size exclusion chromatography, the chromatography column having been calibrated using polystyrene standards. It is then sufficient to verify that the chromatogram has no signal corresponding to lower molar masses than 800 g/mol.

Gas phase chromatography with external standard can be used to assay compounds comprising an isosorbide unit such as IMGE or IDGE.

To identify compounds with higher molar masses, in particular oligomers comprising two or three isosorbide units, such as DGEDIG or DGETIDG, mass spectroscopy analysis techniques can be used. Mention will in particular be made of techniques of the MALDI (matrix assisted laser desoprtion ionization), LC-MC (liquid chromatography-mass spectrometry), or ESI MS (electrospray ionization mass spectrometry) types.

Preferably, the number-average molar mass (Mn) of the compounds comprising isosorbide units comprised in the epoxy pre-polymer according to the invention is greater than 1000 g/mol, preferably between 1000 and 8000 g/mol.

The tests described in the "examples" part of the present document were made on epoxy pre-polymers comprising essentially compounds comprising isosorbide units. In these tests, when the Mn of the epoxy pre-polymer is greater than 1000 g/mol, the epoxy pre-polymer is not mutagenic.

Preferably, the epoxy pre-polymer according to the invention has a Mn of greater than 1000 g/mol, preferably between 1000 and 8000 g/mol.

Mn of less than 8000 g/mol correspond to oligomeric compositions, which are easier to handle than polymeric compositions.

Preferably, the Mn referred to in the present document correspond to Mn measured by size exclusion chromatography, the chromatography column having been calibrated using polystyrene standards.

Preferably, the epoxy pre-polymer according to the invention has an EEW of less than 1000 g/eq, more preferentially between 230 and 1000 g/eq. and even more preferentially between 300 and 600 g/eq.

Epoxy pre-polymers comprising very low EEW isosorbide units may correspond to epoxy pre-polymers with a high IDGE content and/or compounds comprising low molar mass isosorbide units. In practice, the epoxy pre-polymers comprising isosorbide units of EEW of less than 230 g/eq have very high chances of having too high a mutagenic potential.

Preferably, the epoxy pre-polymer according to the invention comprises glycidyl ether groups.

Preferably, the epoxy pre-polymer according to the invention comprises glycidyl ether groups carried by isosorbide units.

Preferably, the epoxy pre-polymer according to the invention comprises glyceryl units.

The glyceryl units are generally present in the oligomers present in the epoxy pre-polymers comprising isosorbide units.

Preferably, the epoxy pre-polymer according to the invention comprises glycidyl ether groups carried by glyceryl units.

In the oligomers present in the epoxy pre-polymers comprising isosorbide units, glyceryl units usually have free hydroxyl functions. In order to reduce the EEW of the epoxy pre-polymers comprising oligomers, these free hydroxyl functions can be refunctionalized with epoxidized groups such as glycidyl ether groups. This results in epoxy pre-polymers comprising glycidyl ether groups carried by glyceryl units.

Preferably, the epoxy pre-polymer according to the invention is an isosorbide-based epoxy pre-polymer.

For example, the epoxy pre-polymer according to the invention is an isosorbide-based epoxy pre-polymer based wherein at least 10%, preferentially at least 30%, more preferentially at least 50%, even more preferentially at least 80% of the glycidyl ether groups are borne by isosorbide units or by glyceryl units which themselves are linked to isosorbide units.

Preferably, the epoxy pre-polymer according to the invention comprises between 5 and 85%, more preferentially between 5 and 75%, even more preferentially between 30 and 70% by weight of isosorbide units relative to the total weight of the epoxy pre-polymer.

There are thus epoxy pre-polymers with high content of biosourced units.

According to one embodiment, the epoxy pre-polymer according to the invention comprises a polyol unit different from the isosorbide unit and different from the glyceryl unit, for example chosen from the following non-limiting list of alcohol units:

Pentaerythritol,
Trimethylol ethane,
Trimethylol propane,
Spiroglycol,
Tricyclodecanedimethanol,
Ethylene glycol,
Propylene glycol,
Pentan-1,5-diol,
Hexan-1,6-diol,
$C_x$ aliphatic diols, where $x \geq 7$,
1,y-cyclohexanedimethanol, where y=2, 3 or 4,
Furan-i,j-dimethanol, where $\{i,j\}=\{1,4\}$, $\{1,3\}$ or $\{2,3\}$,
Thiophen-i,j-dimethanol, where $\{i,j\}=\{1,4\}$, $\{1,3\}$ or $\{2,3\}$.

Preferably, the polyol unit different from the isosorbide unit is a diol unit, for example a diol unit chosen from the diol units cited in the preceding list.

More preferentially, the polyol unit different from the isosorbide unit is a 1,4-cyclohexanedimethanol unit.

For example, the epoxy pre-polymer according to the invention comprises between 5 and 80%, preferentially between 20 and 60% by mol of different polyol units of the isosorbide unit and different from the glyceryl unit relative to the amount of isosorbide units comprised in the epoxy pre-polymer.

For example, if the epoxy pre-polymer according to the invention comprises 50% by mol of different polyol units of the isosorbide unit and different from the glyceryl unit relative to the amount of isosorbide units comprised in the epoxy pre-polymer, then this means that said epoxy pre-polymer comprises twice as many moles of isosorbide units as moles of different polyol units of the isosorbide unit and different from the glyceryl unit. The same is true with 20% and five times more.

According to another aspect of the present invention, a curable composition is proposed comprising the epoxy pre-polymer according to the invention, characterized in that it further comprises at least one accelerating agent and/or at least one curing agent.

"Curable composition" is intended to mean a liquid mixture that is capable of polymerizing to form a cross-linked (cured) resin. For example, a curable composition comprising an epoxy pre-polymer is a liquid mixture capable of polymerizing to form a polyepoxide, which by definition is a crosslinked resin.

The curable composition may, for example, comprise a curing agent. The system {epoxy pre-polymer, curing agent} can then be stoichiometric or contain an excess of reactive functions of the curing agent or an excess of epoxy functions.

According to another aspect of the present invention, a polyepoxide is proposed, obtained by curing the curable composition according to the invention.

Curing (that is, crosslinking) of the curable composition according to the invention can occur spontaneously or else require heating or irradiation by UV radiation.

The heating may, for example, be a curing cycle optionally including a period at room temperature followed by one or several periods of heating at increasing temperatures and comprised between 30° C. and 260° C.

According to another aspect of the present invention, a composite material, coating, or adhesive is proposed comprising the polyepoxide according to the invention.

The composite materials according to the invention may be composite materials of the {polyepoxide; fibers} type, the fibers of which especially may be selected from glass fibers, carbon fibers, basalt fibers, plant fibers (flax, hemp).

The composite materials according to the invention may be useful for manufacturing parts with structural performance capabilities, such as, for example, in the automotive field, the nautical field, the aeronautics field or even in the sports and leisure field.

According to another aspect of the present invention, a method for preparing an epoxy pre-polymer according to the invention, comprising the following steps is proposed:

a step a) of providing an epoxy pre-polymer A comprising isosorbide units;
optionally, a step b) and/or a step c), step b) being able to be carried out before step c) or vice versa;
a step d) carried out after any one of the steps a), b) or c);
wherein step b) comprises a step of reaction between a polyol and the epoxy pre-polymer A or the epoxy pre-polymer C obtained at the end of step c) or the epoxy pre-polymer D obtained at the end of step d) so as to obtain an epoxy pre-polymer B comprising isosorbide units of Mn greater than that of the epoxy pre-polymer A, C or D respectively,
wherein step c) comprises a step of refunctionalizing the epoxy pre-polymer A or the epoxy pre-polymer B or the epoxy pre-polymer D obtained at the end of step d) so as to obtain an epoxy pre-polymer C comprising isosorbide units having an EEW less than that of the epoxy pre-polymer A, B or D respectively,
wherein step d) comprises a step of purification of the epoxy pre-polymer A, B or C making it possible to reduce the isosorbide diglycidyl ether content of the epoxy pre-polymer A, B or C.

The epoxy pre-polymer A during step a) can be provided through synthesis. If so, it is not limited to a particular method of synthesis. It can be any epoxy pre-polymer synthesis method comprising isosorbide units known in the prior art, for example the methods described in the documents cited above.

The epoxy pre-polymer A may be variably rich in oligomers.

The literature discloses various techniques that allow the formation of oligomers rich in oligomers. These techniques have mainly been developed for epoxy pre-polymers based on bisphenol A.

One of these techniques consists of reacting an epoxy pre-polymer with a low molar mass with a diol making it possible, by reaction between the epoxy group of the pre-polymer and the hydroxyl functions of the diol, to oligomerize the mixture and to increase its molecular weight (Fusion process).

Step b) comprises performing a Fusion process.

Another technique, called the Taffy process, consists of a direct synthesis of oligomers by a reaction between a diol and a limited amount of epichlorohydrin or another reagent allowing the introduction of epoxide functions.

In the Taffy process, due to the limited amount of epichlorohydrin, the hydroxyl functions of the diol are partly available to react in ring-opening reactions of epoxide rings already carried by diol units, which promotes the formation of oligomers.

According to certain embodiments, the method for preparing an epoxy pre-polymer according to the invention can combine a step corresponding to the Fusion process with a step corresponding to the Taffy process. This corresponds to the case where the method according to the invention comprises both a step a) implementing a Taffy process and a step b).

The method according to the invention can comprise a step c) comprising the refunctionalization of an epoxy pre-polymer making it possible to obtain epoxy pre-polymers according to the invention having a relatively low EEW despite the presence of oligomers in the epoxy pre-polymer.

The method according to the invention comprises a step d) comprising a step of purification of an epoxy pre-polymer making it possible to reduce the IDGE content of said epoxy pre-polymer.

The steps b) and c) being optional and able to be carried out one before the other or vice versa and step d) being able to be carried out after any one of the steps a), b) or c), the method according to the invention may comprise any one of the following sequence sequences:
  step a) then step d),
  step a) then step b) then step d),
  step a) then step d) then step b),
  step a) then step c) then step d),
  step a) then step d) then step c),
  step a) then step b) then step c) then step d),
  step a) then step b) then step d) then step c),
  step a) then step d) then step b) then step c),
  step a) then step c) then step b) then step d),
  step a) then step c) then step d) then step b),
  step a) then step d) then step c) then step b).

According to a preferred embodiment of the method according to the invention, the method according to the invention may comprise any one of the following sequences:
  step a) then step d),
  step a) then step b) then step d),
  step a) then step d) then step b),
  step a) then step d) then step c),
  step a) then step b) then step d) then step c), step a) then step d) then step b) then step c),
  step a) then step d) then step c) then step b).

According to an even more preferred embodiment of the method according to the invention, the method according to the invention may comprise any one of the following sequences:
  step a) then step d),
  step a) then step b) then step d),
  step a) then step d) then step b),
  step a) then step b) then step c) then step d),
  step a) then step b) then step d) then step c),
  step a) then step d) then step b) then step c).

According this last embodiment, the method for preparing an epoxy prepolymer according to the invention comprises the following steps:
  a step a) of providing an epoxy pre-polymer A comprising isosorbide units;
  optionally, a step b) or a step b) and a step c), step b) being carried out before step c) when the method comprises a step b) and a step c);
  a step d) carried out after any one of the steps a), b) or c); wherein step b) comprises a step of reaction between a polyol and the epoxy pre-polymer A or the epoxy pre-polymer D obtained at the end of step d) so as to obtain an epoxy pre-polymer B comprising isosorbide units of Mn greater than that of the epoxy pre-polymer A or D respectively, wherein step c) comprises a step of refunctionalizing the epoxy pre-polymer B or the epoxy pre-polymer D obtained at the end of step d) so as to obtain an epoxy pre-polymer C comprising isosorbide units having an EEW less than that of the epoxy pre-polymer B or D respectively,
    wherein step d) comprises a step of purification of the epoxy pre-polymer A, B or C making it possible to reduce the isosorbide diglycidyl ether content of the epoxy pre-polymer A, B or C).

Preferably, step d) is carried out as the last one of the steps a), b), c) and d). This makes it possible to increase the efficiency of the method.

According to one embodiment, in the method according to the invention, step a) comprises a step of reaction between:
  isosorbide,
  from 2 to 3 equivalents of epichlorohydrin relative to the amount of isosorbide, and
  from 2 to 2.5 equivalents of a $1^{st}$ basic reagent relative to the amount of isosorbide.

Preferably, the $1^{st}$ basic reagent is selected from lithium, potassium, calcium or sodium hydroxides, more preferentially in the form of an aqueous solution, and even more preferentially an aqueous sodium hydroxide solution.

According to one embodiment, the reaction step between isosorbide, epichlorohydrin and the basic reagent included in step a) is carried out in the presence of an amount of phase-transfer catalyst of between 0.01 and 1% by weight relative to the weight of isosorbide, preferably the phase-transfer catalyst is chosen from tetraalkyl ammonium halides, sulfates or hydrogen sulfates, more preferentially from the compounds having the following formula: $X^-R_4N^+$, where $X^-$ is selected from $Cl^-$, $Br^-$, or $I^-$ and where R is selected from ethyl, propyl, or butyl groups, even more preferentially, the phase transfer catalyst is selected from tetraethylammonium bromide, tetrabutylammonium bromide, or tetrabutylammonium iodide.

For example, the amount of phase transfer catalyst in step a) is between 0.01 and 0.2% by weight relative to the weight of isosorbide.

For example, the amount of phase transfer catalyst in step a) is between 0.2 and 0.4% by weight relative to the weight of isosorbide.

For example, the amount of phase transfer catalyst in step a) is between 0.4 and 0.6% by weight relative to the weight of isosorbide.

For example, the amount of phase transfer catalyst in step a) is between 0.6 and 0.8% by weight relative to the weight of isosorbide.

For example, the amount of phase transfer catalyst in step a) is between 0.8 and 1% by weight relative to the weight of isosorbide.

The addition of phase transfer catalyst makes it possible to limit the formation of oligomers for the same amount of epichlorohydrin. The less phase transfer catalyst there is, the longer the oligomers are on average and the more oligomers there are.

According to one embodiment, the reaction step between isosorbide, epichlorohydrin and the $1^{st}$ basic reagent included in step a) is done in the absence of a phase transfer catalyst.

According to one embodiment, in the method according to the invention, step b) of reaction between the polyol and the epoxy pre-polymer A, C or D comprises the reaction under an inert atmosphere, at a temperature of between 150° C. and 180° C., between the epoxy pre-polymer A, C or D and the polyol in the presence of an amount of one $2^{nd}$ basic reagent comprised between 0.1% and 2% by weight relative to the mass of the epoxy pre-polymer A, C or D respectively, preferably the $2^{nd}$ basic reagent is selected from lithium, potassium, calcium or sodium hydroxides, and is more preferentially sodium hydroxide.

For example, according to this embodiment, the reaction between the polyol and the epoxy pre-polymer A, C or D can be carried out in the presence or absence of a phase transfer catalyst.

The addition of phase transfer catalyst in step b) accelerates the reaction. The phase transfer catalyst also makes it possible to better control the formation of oligomers.

According to one embodiment, in the method according to the invention, the polyol which reacts in step b) is a diol, preferably the diol is chosen from the following diols:

Isosorbide
Isoidide
Isomannide
Spiroglycol,
Tricyclodecanedimethanol,
Ethylene glycol,
Propylene glycol,
Pentan-1,5-diol,
Hexan-1,6-diol,
$C_x$ aliphatic diols, where x≥7,
1,y-cyclohexanedimethanol, where y=2, 3 or 4,
Furan-i,j-dimethanol, where {i,j}={1,4}, {1,3} or {2,3},
Thiophen-i,j-dimethanol, where {i,j}={1,4}, {1,3} or {2,3}, and
mixtures thereof;

more preferentially, the diol is 1,4-cyclohexanedimethanol or isosorbide.

The choice of the polyol influences the kinetics of step b) and also plays a role in the physical and chemical properties of the polyepoxide obtained from the epoxy pre-polymer.

It may in particular be advantageous to use a polyol capable of accelerating the kinetics of step b) in order to limit the hydrolysis of the epoxide functions and to maintain a relatively low EEW.

According to one embodiment, in the method according to the invention, step c) of refunctionalization comprises a step of reaction between:
the epoxy pre-polymer A, B or D,
from 4 to 6 equivalents of epichlorohydrin relative to the amount of hydroxyl functions present in the epoxy pre-polymer A, B or D, and
from 0.8 to 1.2 equivalents of one $3^{rd}$ basic reagent with respect to the amount of hydroxyl functions present in the epoxy pre-polymer A, B or D.

The amount of hydroxyl functions in the epoxy pre-polymer may for example be determined by $^1$H NMR in DMSO, by integrating the signal corresponding to the alcohol OH.

Preferably, the $3^{rd}$ basic reagent is selected from lithium, potassium, calcium or sodium hydroxides, more preferentially in the form of an aqueous solution, and even more preferentially an aqueous sodium hydroxide solution.

Preferably, in the method according to the invention, the step of purification comprises a membrane purification step, preferably the membrane purification step comprises a dialysis step, a nanofiltration step, or an ultrafiltration step.

Preferably, the membrane purification step is carried out with a membrane (for example included in a dialysis filter or tube) having a cutoff threshold of 1000 g/mol.

Preferably, step d) comprises dissolving in an organic or aqueous solvent the epoxy pre-polymer A, B or C before the membrane purification step, more preferentially the solution is dissolved in the form of an aqueous solution comprising between 10% and 50% by weight of the epoxy pre-polymer A, B or C relative to the total weight of the aqueous solution comprising the epoxy pre-polymer A, B or C.

According to another aspect of the present invention, an alternative method for preparing an epoxy pre-polymer according to the invention, comprising the following steps is proposed:

e) a step of providing a $1^{st}$ epoxy pre-polymer devoid of isosorbide units;
f) a step of reaction between the $1^{st}$ epoxy pre-polymer and isosorbide so as to obtain a $2^{nd}$ epoxy pre-polymer comprising isosorbide and Mn units greater than that of the $1^{st}$ epoxy pre-polymer;
g) optionally a step of refunctionalizing the $2^{nd}$ epoxy pre-polymer so as to obtain a $3^{rd}$ epoxy pre-polymer having an EEW less than that of the $2^{nd}$ epoxy pre-polymer.

According to this alternative method for preparing an epoxy pre-polymer according to the invention, it is ensured that IMGE or IDGE are not formed in any step of the method.

Step e) can be carried out by synthesis, according to any method known to a person skilled in the art. The chemical nature of the $1^{st}$ epoxy pre-polymer devoid of isosorbide units is not otherwise particularly limited.

According to one embodiment, step f) of reaction between the isosorbide and $1^{st}$ epoxy pre-polymer comprises the reaction under an inert atmosphere, at a temperature of between 150° C. and 180° C., between the $1^{st}$ epoxy pre-polymer and isosorbide in the presence of an amount of a 4th basic reagent comprised between 0.1% and 2% by weight relative to the mass of the $1^{st}$ epoxy pre-polymer respectively, preferably $4^{th}$ basic reagent is selected from lithium, potassium, calcium or sodium hydroxides, and is more preferentially sodium hydroxide.

For example, according to this embodiment, the reaction between the isosorbide and the $1^{st}$ epoxy pre-polymer can be carried out in the presence or absence of a phase transfer catalyst.

The addition of phase transfer catalyst in this step f) corresponding to a Taffy process accelerates the reaction and limits the hydrolysis of the epoxide functions, therefore makes it possible to maintain a relatively low EEW.

According to one embodiment, the re-functionalization step g) comprises a reaction step between:
- the $2^{nd}$ epoxy pre-polymer,
- from 4 to 6 equivalents of epichlorohydrin relative to the amount of hydroxyl functions present in $2^{nd}$ epoxy pre-polymer, and
- from 0.8 to 1.2 equivalents of a $5^{th}$ basic reagent with respect to the amount of hydroxyl functions present in the $2^{nd}$ epoxy pre-polymer.

The amount of hydroxyl functions in the epoxy pre-polymer may for example be determined by $^1$H NMR in DMSO, by integrating the signal corresponding to the alcohol OH.

Preferably, the $5^{th}$ basic reagent is selected from lithium, potassium, calcium or sodium hydroxides, more preferentially in the form of an aqueous solution, and even more preferentially an aqueous sodium hydroxide solution.

EXAMPLES

The epoxy equivalent weight (EEW) is measured according to standard ISO 3001 or ASTM D1652.

The number molar masses (Mn) are measured by size exclusion chromatography, the chromatography column having been calibrated using polystyrene standards.

The compositions of the mixtures shown in Tables 1 and 4 and the composition of the oligomeric fraction 1 of Table 6 (see below) were determined by size exclusion chromatography techniques, the chromatography column having been calibrated using polystyrene standards, as well as by gas chromatography with external standards and by weight spectrometry techniques.

Example 1: Synthesis of Oligomer-Rich Isosorbide-Based Epoxy Pre-Polymers by the Fusion Process

Step 1: Synthesis of a First Isosorbide-Based Epoxy Pre-Polymer According to the Prior Art Isosorbide, epichlorohydrin (5 molar equivalents relative to the isosorbide) and tetraethylammonium bromide (TEAB, 1% by weight relative to the mass of isosorbide) are introduced into a double jacketed reactor, equipped with a reverse Dean-Stark apparatus. The medium is stirred and heated to a temperature of 80° C. under a partial vacuum of 275 mbar. After distillation of an amount of epichlorohydrin sufficient to fill the reverse Dean-Stark apparatus, an aqueous solution of sodium hydroxide at 50% by weight (2.1 equivalents in mol relative to the amount of isosorbide) is introduced dropwise and over a period of 3 hours. During the addition of sodium sulfate, the distillation of the water-epichlorohydrin azeotrope occurs and the demixing in the Dean-Stark allows the water introduced and formed during the reaction to be removed. Once the addition of sodium hydroxide is complete, the medium is stirred at 80° C. for 1 hour so as to finish removing the water from the reaction medium. The heating is then cut off and the medium is allowed to cool in air at room temperature. The medium is then stripped, and the salts formed during the reaction are filtered using a sintered glass. The salt cake is then washed using epichlorohydrin. The filtrate is recovered. The washing epichlorohydrin and the residual epichlorohydrin are removed using a rotary evaporator. The results of the analyses carried out on the obtained epoxy prepolymer are presented in Table 1.

TABLE 1

| $1^{st}$ epoxy pre-polymer | Isosorbide (% w) | IMGE (% w) | IDGE (% w) | Oligomers (% w) | EEW (g/eq) | Mn (g/mol) |
|---|---|---|---|---|---|---|
| I1 | nd | 1.1 | 54.4 | 44.5 | 161 | 332 |

Step 2: Oligomerization of the First Epoxy Pre-Polymer Obtained in Step 1

The aim of this step is to increase the chain length of the first epoxy pre-polymer obtained in step 1. A second epoxy pre-polymer is thus obtained.

200 g of the first epoxy pre-polymer are introduced into a double jacketed reactor equipped with mechanical stirring. The first epoxy pre-polymer is heated to 80° C. under an inert nitrogen atmosphere. A defined mass proportion of diol (isosorbide or CHDM) is added under nitrogen. The medium is stirred until a homogeneous medium is obtained. A defined amount of catalyst (sodium hydroxide in the form of an aqueous solution at 50% by weight, with addition or not of phase transfer catalyst, TEAB) is added under nitrogen. The medium is then heated at 180° C. for a given time. Once the reaction is complete, the medium is allowed to cool to air in order to reach a temperature of 80° C. The medium is removed from the reactor and the salts formed by the catalyst are filtered at 80° C. The results of the analyses carried out on the epoxy pre-polymers obtained are presented in Table 2.

TABLE 2

| $2^{nd}$ epoxy pre-polymer | % diol | reaction time (hours) | % NaOH | % TEAB | EEW (g/eq.) | Mn (g/mol) |
|---|---|---|---|---|---|---|
| I2A | 30 (isosorbide) | 12 | 0.5 | 0 | 831 | 734 |
| I2B | 30 (isosorbide) | 6 | 0.5 | 1 | 1024 | 834 |
| I2C | 30 (CHDM) | 3 | 0.5 | 0 | 317 | 623 |
| I2D | 20 (CHDM) | 6 | 0.5 | 0 | 309 | 720 |

The percentages are mass percentages relative to the mass of the first epoxy pre-polymer introduced.

Step 3: Refunctionalization of the Second Epoxy Pre-Polymer Obtained in Step 2

With the aim of ensuring the reactivity of the second epoxy pre-polymer, it may be necessary to replace the hydroxyl functions of said second epoxy pre-polymer with glycidyl ether groups and thus obtain a third epoxy pre-polymer whose EEW is less than the EEW of the second epoxy pre-polymer.

For this, 200 g of the second epoxy pre-polymer are redissolved in a reactor equipped with a distillation system such as that of step 1 in 5 equivalents of epichlorohydrin relative to the hydroxyl functions of the oligomeric resin (the amount of hydroxyl functions is determined by 1H NMR in DMSO, by integrating the signal corresponding to the alcohol OH). The medium is heated to 80° C. and the pressure is lowered to 275 mbars until the boiling and distillation of the epichlorohydrin. 1 equivalent of sodium hydroxide (relative to the hydroxyl functions, in the form of an aqueous solution at 50% by weight) is then added over a period of three hours using a peristaltic pump. The azeotrope is distilled during the addition and the epichlorohydrin is reintroduced into the reaction medium using the reverse Dean-Stark apparatus. Once the addition is complete, the medium is left under distillation until the water is completely removed from the reaction medium. Heating is stopped and the reaction medium is allowed to cool in air at room temperature.

The salts are filtered on sintered glass and washed using 50 mL of epichlorohydrin. The filtrate is recovered. The washing epichlorohydrin and the residual epichlorohydrin are distilled under reduced pressure using a rotary evaporator. The results of the analyses carried out on the obtained epoxy pre-polymers are presented in Table 3.

TABLE 3

| Starting epoxy pre-polymer | Refunctionalized epoxy pre-polymer | EEW (g/eq.) | Mn (g/mol) |
|---|---|---|---|
| I2A | I3A | 347 | 1100 |
| I2B | I3B | 375 | 960 |

Table 3 gives the characteristics of the refunctionalized epoxy pre-polymers and for each refunctionalized epoxy pre-polymer prepared, the epoxy pre-polymer from which it was prepared.

Example 2: Synthesis of Oligomer-Rich Isosorbide-Based Epoxy Pre-Polymers by the Taffy Process Isosorbide, epichlorohydrin (3 equivalents in mol relative to the amount of isosorbide), and also a known quantity of TEAB, are introduced into a double jacketed reactor equipped with a reverse Dean Stark apparatus. The medium is stirred and heated to a temperature of 80° C. under a partial vacuum of 275 mbar. Once the distillation of the epichlorohydrin and the reflux of that compound via the reverse Dean Stark apparatus have begun, 2.1 equivalents in mol of sodium hydroxide (in aqueous solution at 50%) relative to the amount of isosorbide are introduced dropwise over a period of three hours. The distillation of the water-epichlorohydrin azeotrope then occurs and the water thus distilled is removed via the reverse Dean-Stark assembly.

Once the addition of sodium hydroxide is complete, the medium is stirred at 80° C. for one hour so as to finish removing the water from the reaction medium. The medium is then cooled in air at room temperature. The recipe is then filtered on a sintered glass to remove the sodium chloride formed during the reaction. The salts are washed with epichlorohydrin. The filtrate is recovered and the epichlorohydrin is distilled using a rotary evaporator.

The results of the analyses carried out on the obtained epoxy pre-polymers are presented in Table 4.

TABLE 4

| Epoxy pre-polymer | % TEAB | % IDGE in the epoxy pre-polymer | % oligomers in the epoxy pre-polymer | EEW (g/eq.) | Mn (g/mol) |
|---|---|---|---|---|---|
| II1A | 1 | 34 | 66 | 195 | 450 |
| II1B | 0.5 | 38 | 62 | 193 | 510 |
| II1C | 0 | 22.5 | 77.5 | 215 | 650 |

The percentages are mass percentages. The percentage of TEAB is given relative to the mass of isosorbide introduced. The percentages of IDGE and oligomers are given relative to the total weight of the epoxy pre-polymer.

Example 3: Purification of the Epoxy Pre-Polymers by Membrane Purification

In order to reduce the content of compounds of low molar mass in the synthesized epoxy pre-polymers, membrane purification by dialysis or ultrafiltration has been carried out.

Dialysis 5 g of epoxy pre-polymer are inserted into a dialysis tube having a cutoff threshold at 1000 g/mol. The tube is hermetically sealed and placed in a beaker filled with 5 L of demineralized water. The aqueous medium is stirred using a magnetic bar at room temperature for 24 hours. During these 24 hours, the water from the beaker is changed 2 times.

After the 24 hours of treatment, the dialysis tube is recovered and emptied into a flask. The water is evaporated under reduced pressure to arrive at an epoxy pre-polymer having a reduced content of compounds of low molar mass.

Ultrafiltration

For ultrafiltration, a membrane having a cutoff threshold of 1000 g/mol is used. The separation is carried out starting from an aqueous solution containing 20% by weight of epoxy pre-polymer.

The results of the analyses carried out on the obtained epoxy pre-polymers are presented in Table 5.

TABLE 5

| Starting epoxy pre-polymer | Technique used | Epoxy pre-polymer obtained after membrane purification | EEW (g/eq.) | Mn (g/mol) |
|---|---|---|---|---|
| I2A | Dialysis | III1 | 1024 | 1500 |
| II1A | Dialysis | III2 | 308 | 1200 |
| II1C | Dialysis | III3 | 591 | 1700 |
| I3A | Dialysis | III4 | 505 | 3800 |
| I2D | Dialysis | III5 | 495 | 1600 |
| I2A | Ultrafiltration | III6 | 1075 | 1600 |
| II1B | Ultrafiltration | III7 | 307 | 1200 |

Table 5 gives the characteristics (EEW and Mn) of the epoxy pre-polymers obtained after membrane purification and for each epoxy pre-polymer obtained by membrane purification, the epoxy pre-polymer from which it was prepared and the membrane purification technique used.

Example 4: Toxicological Evaluation of Epoxy Pre-Polymers

In order to determine the mutagenic potential of the epoxy pre-polymers, an Ames test was carried out on different Mn and EEW epoxy resins. The results are expressed in induction levels, that is, the number of mutant bacterial colonies obtained from a given strain exposed to the compound. The resin is considered to be non-toxic in the case of an induction ratio of 2 or less. The results are as follows: The results of the Ames tests are presented in Table 6.

TABLE 6

| Epoxy pre-polymer | EEW (g/eq.) | Mn (g/mol) | Induction ratio |
|---|---|---|---|
| IDGE 1* fraction | 130 | 258 | 20.2 |
| I1 | 169 | 338 | 12.1 |
| I1C | 215 | 650 | 9.9 |
| Oligomer 1** fraction | 265 | 465 | 2.9 |
| I2A | 734 | 835 | 2.4 |
| III2 | 308 | 1200 | <2 |
| III6 | 1076 | 1600 | <2 |
| III5 | 495 | 1600 | <2 |
| III4 | 505 | 3800 | <2 |

*The IDGE 1 fraction is obtained by distillation on a wiped film of the resin I1 obtained in step 1 of example 1, it is composed of 98% IDGE.
**The oligomer fraction 1 corresponds to the distillation residue of the resin I1 produced in order to obtain the IDGE 1 fraction. It is composed of 1.2% IDGE, 40% DGEDIG and glycidyl ether derivatives of DGEDIG and 35% DGETIDG and glycidyl ether derivatives of DGETIDG. It therefore essentially contains short oligomeric chains.

The increase in chain length makes it possible to reduce the mutagenic potential of the epoxy pre-polymers comprising isosorbide units, even to eliminate it when the epoxy pre-polymers are subjected to a membrane purification step by dialysis or by ultrafiltration.

The compounds having an Mn of greater than 1000 g/mol are considered to be non-mutagenic. In addition, the EEW does not influence the mutagenic potential of the epoxy pre-polymer from the moment when the Mn threshold of 1000 g/mol is crossed, allowing the safe use of highly functionalized epoxy oligomers.

The invention claimed is:

1. An epoxy pre-polymer comprising isosorbide units, wherein it comprises less than 1%; by weight of isosorbide diglycidyl ether, relative to the total weight of the epoxy pre-polymer, and wherein the number-average molar mass of the compounds comprising isosorbide units comprised in the epoxy pre-polymer is greater than 1000 g/mol.

2. The epoxy pre-polymer according to claim 1, wherein the compounds comprising isosorbide units having a molar mass of less than 300 g/mol represent less than 1% by weight relative to the total weight of the pre-polymer.

3. The epoxy pre-polymer according to claim 1, wherein the number-average molar mass of the epoxy pre-polymer is greater than 1000 g/mol.

4. The epoxy pre-polymer according to claim 1, wherein the EEW of the epoxy pre-polymer is less than 1000 g/eq.

5. The epoxy pre-polymer according to claim 1, comprising glycidyl ether groups.

6. The epoxy pre-polymer according to claim 5 comprising glycidyl ether groups carried by isosorbide units.

7. The epoxy pre-polymer according to claim 5, wherein at least 5%; of the glycidyl ether groups are borne by isosorbide units or by glyceryl units which themselves are linked to isosorbide units.

8. The epoxy polymer according to claim 1, comprising between 5 and 85%; by weight of isosorbide units relative to the total weight of the epoxy pre-polymer.

9. A curable composition comprising the epoxy pre-polymer of claim 1, further comprising a curing agent and/or an accelerating agent.

10. A polyepoxide obtained by curing the curable composition according to claim 9.

11. A composite material, coating or adhesive comprising the polyepoxide according to claim 10.

12. A method for preparing an epoxy pre-polymer according to claim 1 comprising the following steps:
   a step a) of providing an epoxy pre-polymer A comprising isosorbide units;
   optionally, a step b) and/or a step c), step b) being able to be carried out before step c) or vice versa;
   a step d) carried out after any one of the steps a), b) or c);
   wherein step b) comprises a step of reaction between a polyol and the epoxy pre-polymer A or the epoxy pre-polymer C obtained at the end of step c) or the epoxy pre-polymer D obtained at the end of step d) so as to obtain an epoxy pre-polymer B comprising isosorbide units of Mn greater than that of the epoxy pre-polymer A, C or D respectively,
   wherein step c) comprises a step of refunctionalizing the epoxy pre-polymer A or the epoxy pre-polymer B or the epoxy pre-polymer D obtained at the end of step d) so as to obtain an epoxy pre-polymer C comprising isosorbide units having an EEW less than that of the epoxy pre-polymer A, B or D respectively,
   wherein step d) comprises a step of purification of the epoxy pre-polymer A, B or C making it possible to reduce the isosorbide diglycidyl ether content of the epoxy pre-polymer A, B or C.

13. A method according to claim 12, wherein the step of purification comprises a membrane purification step.

14. A method for preparing an epoxy pre-polymer according to claim 1 comprising the following steps:
   e) a step of providing a $1^{st}$ epoxy pre-polymer devoid of isosorbide units;
   f) a step of reaction between the $1^{st}$ epoxy pre-polymer and isosorbide so as to obtain a $2^{nd}$ epoxy pre-polymer comprising isosorbide units and having a Mn greater than that of the $1^{st}$ epoxy pre-polymer;
   g) optionally a step of refunctionalizing the $2^{nd}$ epoxy pre-polymer so as to obtain a 3rd epoxy pre-polymer having an EEW less than that of the $2^{nd}$ epoxy pre-polymer.

* * * * *